United States Patent [19]

Hutson

[11] Patent Number: 4,495,418

[45] Date of Patent: Jan. 22, 1985

[54] METHOD OF STANDARDIZING IR BREATH ALCOHOL DEVICE

[75] Inventor: Donald G. Hutson, El Cerrito, Calif.

[73] Assignee: Cal Detect, Inc., Richmond, Calif.

[21] Appl. No.: 466,434

[22] Filed: Feb. 15, 1983

[51] Int. Cl.³ .......................... G01F 15/14; G01J 5/02
[52] U.S. Cl. .................................................... 250/343
[58] Field of Search ................. 250/343; 436/132, 900

[56] References Cited

U.S. PATENT DOCUMENTS

| 3,847,551 | 11/1974 | Hutson | 436/132 X |
| 4,278,636 | 7/1981 | Voight et al. | 436/132 X |
| 4,363,635 | 12/1982 | Hutson | 436/132 |

FOREIGN PATENT DOCUMENTS 2720636  11/1978  Fed. Rep. of Germany ...... 250/343

OTHER PUBLICATIONS

Edward J. Bartosczek, Charles J. Mackley and David M. Gardner, "Infrared Cell for Reactive Gases", *Applied Spectroscopy*, vol. 21, No. 1, (1967), pp. 44–45.

Primary Examiner—Janice A. Howell
Assistant Examiner—Constantine Hannaher
Attorney, Agent, or Firm—Polster, Polster & Lucchesi

[57] ABSTRACT

An IR cell for the detection and measurement of breath alcohol is standardized by passing a dry gas carrier containing a known amount of alcohol through an IR cell the walls exposed to the standardizing mixture of which are, as to the alcohol, non-adsorbent.

4 Claims, 1 Drawing Figure

METHOD OF STANDARDIZING IR BREATH ALCOHOL DEVICE

BACKGROUND OF THE INVENTION

It has become common to standardize chromatographic and fuel cell type breath alcohol measuring devices with a dry standard gas, particularly a gas of the type described in Hutson U.S. Pat. No. 3,847,551. However, this type of standardizing gas has not worked well with IR (infrared) detectors of the type commonly used heretofore. Such IR detectors are well known and will not be described in detail. See, for example, U.S. Pat. No. 4,363,635. In these conventional IR detectors, the cell walls were usually anodized aluminum, with a coating of aluminum oxide on them, or occasionally steel on which rust forms. These metal oxides characteristically adsorb water and alcohol. When the conventional standardizing mixture of humid air and alcohol is used, the water vapor is adsorbed, and the alcohol measured, so that, for a given temperature, reproducable results can be obtained under the proper conditions (but see the description in U.S. Pat. Nos. 3,847,551, and 4,278,636). With a dry carrier, I have discovered that the alcohol itself is adsorbed, leading to erratic results.

One of the objects of this invention is to provide a method of standardizing IR cells by which dry standardizing gas can be utilized.

Other objects will become apparent to those skilled in the art in the light of the following description and accompanying drawing.

SUMMARY OF THE INVENTION

In accordance with this invention, generally stated, a method of standardizing, calibrating or testing an IR cell for the detection and measurement of breath alcohol is provided that comprises passing a standardizing gas consisting of a dry gas carrier containing a known amount of alcohol through an IR cell the walls exposed to the standardizing gas of which are, as to the alcohol, non-adsorbent.

DESCRIPTION OF THE PREFERRED EMBODIMENT

Figure 1:
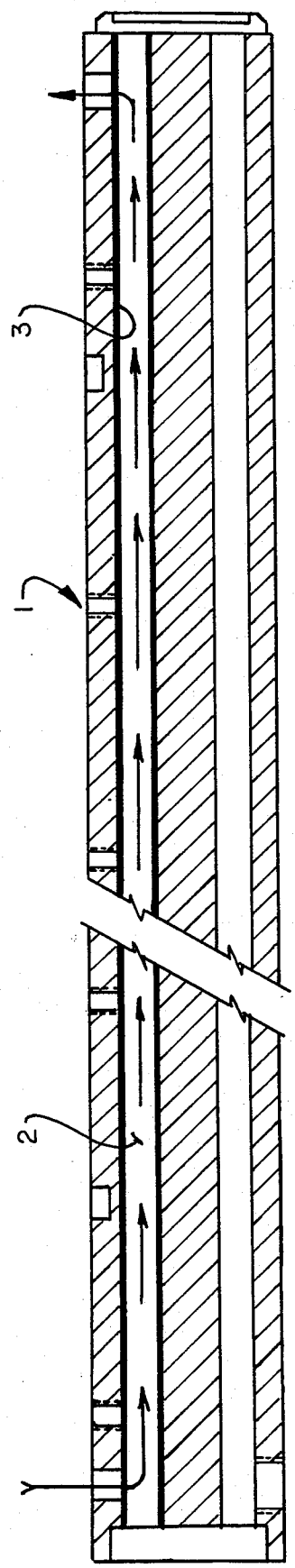
FIG. 1 is a somewhat diagramatic cross-sectional view, broken for convenience, of an IR gas cell made in accordance with one embodiment of this invention.

Referring now to the drawing, reference numeral 1 indicates an IR gas cell, standard except for a coating of nickel 3 on the surfaces defining a passage through which an alcohol standard gas sample is to pass. The path of the gas sample is indicated by arrows.

In the preferred embodiment of this invention, the interior surfaces of the IR cell that are to be exposed to breath samples in a breath analyzer used in connection with determining breath alcohol content are plated with nickel. The analyzer is standardized, calibrated or tested by passing through it a gas sample consisting essentially of anhydrous argon and a known quantity, preferably between 50 and 5,000 parts per million, ethyl alcohol.

The exposed walls can alternatively be made of stainless steel, or can be plated with or formed of other metals, such, for example, as gold or chromium, that are non-adsorptive of alcohol.

I claim:

1. The method of standardizing, calibrating or testing apparatus utilizing an IR cell for determining quantitatively the content of alcohol in breath comprising passing a dry gas carrier sample containing a known amount of ethyl alcohol through an IR cell the walls exposed to said sample of which are, as to said alcohol, non-adsorbant.

2. The method of claim 1 wherein the dry gas is anhydrous argon.

3. The method of claim 1 wherein the said walls are nickel plated.

4. The method of claim 1 wherein the said walls are of stainless steel.

* * * * *